(12) United States Patent
Moore et al.

(10) Patent No.: US 7,164,041 B1
(45) Date of Patent: Jan. 16, 2007

(54) FLUORINATED GEMINI SURFACTANTS

(75) Inventors: George G. I. Moore, Afton, MN (US); Michael S. Terrazas, Prescott, WI (US)

(73) Assignee: 3M Innovative Properties Company, St. Paul, MN (US)

( * ) Notice: Subject to any disclaimer, the term of this patent is extended or adjusted under 35 U.S.C. 154(b) by 0 days.

(21) Appl. No.: 11/281,745

(22) Filed: Nov. 17, 2005

(51) Int. Cl.
C07C 303/00 (2006.01)
B01D 12/00 (2006.01)
A61K 7/48 (2006.01)
C11D 9/00 (2006.01)

(52) U.S. Cl. .................. 564/82; 516/198; 516/203; 510/159; 510/504

(58) Field of Classification Search .................. 564/82; 516/198, 203; 510/159, 504
See application file for complete search history.

(56) References Cited

U.S. PATENT DOCUMENTS

| | | | |
|---|---|---|---|
| 3,906,027 A | 9/1975 | Muessdoerffer et al. |
| 4,167,639 A | 9/1979 | Billenstein et al. |
| 4,823,873 A | 4/1989 | Karydas |
| 4,841,090 A | 6/1989 | Patel |
| 5,342,986 A | 8/1994 | Pohmer et al. |
| 5,502,251 A | 3/1996 | Pohmer et al. |
| 5,591,804 A | 1/1997 | Coggio et al. |
| 5,688,884 A | 11/1997 | Baker et al. |
| 6,200,369 B1 | 3/2001 | Schwarz |
| 6,664,354 B1 | 12/2003 | Savu et al. |

FOREIGN PATENT DOCUMENTS

JP 2004-143145 5/2004

OTHER PUBLICATIONS

Kissa, "Fluorinated Surfactants—Synthesis-Properties-Applications, Chapter 8 Applications", Marcel Dekker, Inc., New York, 1994, pp. 325-327, 343.

Menger et al., "Gemini Surfactants", Angew. Chem. Int. Ed., 2000, vol. 39, pp. 1906-1920.

Layn et al., "A theoretical study of Gemini surfactant phase behavior", Journal of Chemical Physics, Oct. 1, 1998, vol. 109, No. 13, pp. 5651-5658.

Oda et al., "Aggregation Properties and Mixing Behavior of Hydrocarbon, Fluorocarbon, and Hybrid Hydrocarbon—Fluorocarbon Cationic Dimeric Surfactants", Langmuir, 2000, vol. 16, pp. 9759-9769.

Kausch et al., "Surface Tension and Adsorption Properties of a Series of Bolaamphiphilic Poly (fluorooexetane)s", Langmuir, 2003, vol. 19, pp. 7182-7187.

Sievert, "Preparation and Characterisation of Buffered Oxide Etchants", Semiconductor Fabtech—8th Ed., ICG Publishing, date believed to be 1998, pp. 135-138.

Weidner et al., "Role of Surface Tension Gradients in Correcting Coating Defects in Corners", Journal of Colloid and Interface Science, 1996, vol. 179, pp. 66-75.

Overdiep, "The Levelling of Paints", Progress in Organic Coatings, 1986, vol. 14, pp. 159-175.

Moore et al., "Compositions of Fluorochemical Surfactants", U.S. Appl. No. 11/215,077, filed Aug. 30, 2005.

*Primary Examiner*—J. Parsa

(57) ABSTRACT

A gemini surfactant represented by the formula:

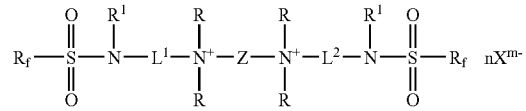

wherein: each $R_f$ independently represents perfluorobutyl or perfluoropropyl; each $R^1$ independently represents alkyl having from 1 to 6 carbon atoms; $L^1$ and $L^2$ represent alkylene having from 2 to 18 carbon atoms; each R represents alkyl having from 1 to 6 carbon atoms; Z represents an organic divalent linking group; and $nX^{m-}$ represents an anion or anions having a charge m, wherein m and n are independently 1 or 2, and wherein the product of n and m is 2. Aqueous compositions containing the gemini surfactant are also disclosed.

15 Claims, No Drawings

FLUORINATED GEMINI SURFACTANTS

BACKGROUND

Gemini surfactants (sometimes called dimeric surfactants) have two hydrophilic groups and two hydrophobic groups in the molecules, in contrast to conventional surfactants that generally have a single hydrophilic group and a single hydrophobic group in the molecule. Gemini surfactants can be ten to a thousand times more surface-active than conventional surfactants with similar but single, hydrophilic and hydrophobic groups in the molecules.

SUMMARY

In one aspect, the present invention provides a gemini surfactant represented by the formula:

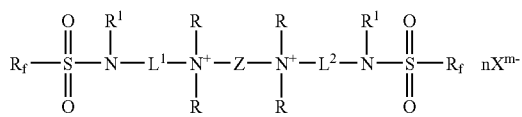

wherein
each $R_f$ independently represents perfluorobutyl or perfluoropropyl;
each $R^1$ independently represents alkyl having from 1 to 6 carbon atoms;
$L^1$ and $L^2$ represent alkylene having from 2 to 18 carbon atoms;
each R represents alkyl having from 1 to 6 carbon atoms;
Z represents an organic divalent linking group; and
$nX^{m-}$ represents an anion or anions having a charge m, wherein m and n are independently 1 or 2, and wherein the product of n and m is 2.

Gemini surfactants according to the present invention are useful, for example, for reducing surface tension of aqueous compositions. In some embodiments, gemini surfactants according to the present invention are useful for enhancing gloss of coated and dried aqueous compositions having dispersed polymer particles.

As used herein:
"alkyl" refers to a monovalent group derived from an alkane by removal of one hydrogen atom;
"alkylene" refers to a divalent group derived from an alkane by removal of two hydrogen atoms;
"aqueous" means containing at least 25 percent by weight of water;
"hydrocarbyl group" refers to a monovalent group derived from a hydrocarbon by removal of a hydrogen atom;
"hydrocarbylene group" refers to a divalent group derived from a hydrocarbon by removal of two hydrogen atoms; and
"perfluoroalkyl group" refers to alkyl group having all of the hydrogen atoms of the alkyl group replaced by fluorine atoms.

DETAILED DESCRIPTION

Gemini surfactants according to the present invention are represented by the formula:

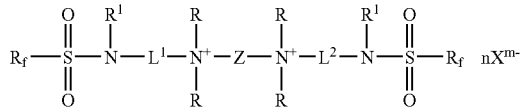

Each $R_f$ independently represents perfluorobutyl (e.g., —$CF_2CF_2CF_2CF_3$ or —$CF_2CF(CF_3)_2$) or perfluoropropyl (e.g., —$CF_2CF_2CF_3$ or —$CF(CF_3)_2$).

Each $R^1$ independently represents alkyl having from 1 to 6 carbon atoms (e.g., methyl, ethyl, propyl, hexyl).

$L^1$ and $L^2$ represent alkylene having from 2 to 4, from 2 to 12, or from 2 to 18 carbon atoms. Examples include ethylene, propylene, butylene, hexylene, 1,12-dodecanediyl, and 1,18-octadecanediyl. L may be linear or branched and may include one or more rings.

Each R represents alkyl having from 1 to 6 carbon atoms (e.g., methyl, ethyl, propyl, hexyl).

Z represents an organic divalent linking group. In some embodiments, Z has from 2 to 10, from 2 to 20, or from 2 to 30 carbon atoms. Examples of suitable organic divalent linking groups include hydrocarbylene groups such as, for example, divalent acyclic aliphatic groups having from 2 to 10, 20, or 30 carbon atoms (e.g., ethylene, propane-1,3-diyl, propane-1,2-diyl, decane-1,10-diyl, tridecane-1,30-diyl); divalent alicyclic groups having from 3 to 10, 20, or 30 carbon atoms (e.g., cyclopropane-1,2-diyl, cyclohexane-1,4-diyl, or bis(1-cyclohexyl-4-yl)propane); divalent mixed aliphatic aromatic groups having from 7 to 15, 20, or 30 carbon atoms (e.g., 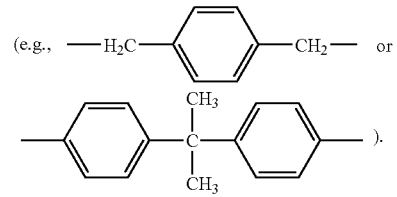).

In some embodiments, Z is selected from the group consisting of divalent hydrocarbylene groups having from 2 to 30 carbon atoms, and combinations of one or more hydrocarbylene groups having from 2 to 30 carbon atoms with at least one of —O— (e.g., —$CH_2CH_2O$— or —$(CH(CH_3)CH_2)O)_{10}$—, —S—, or —$NR^2$— wherein $R^2$ represents H or a hydrocarbyl group having from 1 to 12 carbon atoms (e.g., Z can be —$CH_2CH_2N(CH_3)CH_2CH_2$—).

$nX^{m-}$ represents an anion or anions (e.g., if n=2) having a charge m, wherein m and n are independently 1 or 2, and wherein the product of n and m is 2. Examples of suitable anions include, halides (e.g., chloride, bromide, or iodide), alkanesulfonates (e.g., methanesulfonate trifluoromethanesulfonate); arenesulfonates (e.g., p-toluenesulfonate); hydroxide, alkanecarboxylates (e.g., acetate, fumarate, or tartrate), and complex metal halides (e.g., $BF_4^-$, $SbF_6^-$, or $PF_6^-$).

Typically, to facilitate synthesis, both of $R_f$ groups will be the same, both L groups will be the same, and all of the R groups will be the same, but this is not a requirement.

Convenient synthetic routes to gemini surfactants according to the present invention include formation of the quaternary ammonium salt, for example, by reacting a material represented by the formula $R_fSO_2NR^1$-L-$NR_2$ with a dialkylating agent X-Z-X (e.g., wherein X is monovalent), wherein $R_f$, $R^1$, L, and R are as previously defined. Examples of suitable dialkylating agents include 1,4-bis(chloromethyl)benzene; 1,6-dibromohexane; or 1,11-dichloro-3,6,9-trioxaundecane.

Useful synthetic routes to materials represented by the formula $R_fSO_2NR^1$-L-$NR_2$ include, for example, reacting a material represented by the formula $R_fSO_2NR^1$-L-X with a dialkylamine $R_2NH$. $R_fSO_2NR^1$-L-$NR_2$ can be made by reacting $R_fSO_2NHR^1$ with an aminoalkylating agent such as, for example, $ClC_2H_4N(CH_3)_2$, or an analogous material. $R_fSO_2NR^1$-L-X (e.g., wherein X is Cl or $OSO_2CH_3$) can be made by treatment with thionyl chloride (i.e., $SOCl_2$) or methanesulfonyl chloride (i.e., $CH_3SO_2Cl$) in pyridine from the corresponding alcohol $R_fSO_2NR^1$-L-OH such as, for example, $C_4F_9SO_2N(CH_3)C_nH_{2n}OH$ wherein n is 2 or 4.

The surfactants of the invention are substantially free (i.e. less than 1 wt. %) of fluorochemical compounds that eliminate slowly from living organisms and are therefore considered environmentally sustainable versus most other known commercially available fluorochemical materials, which are based on surfactants containing longer perfluorinated segments or tails.

Many previously known fluorochemical materials contain perfluorooctyl moieties. These surfactants ultimately degrade to perfluorooctyl group-containing compounds. It has been reported that certain perfluorooctyl group-containing compounds may tend to bio-accumulate in living organisms; this tendency has been cited as a potential concern regarding some fluorochemical compounds. For example, see U.S. Pat. No. 5,688,884 (Baker et al.). As a result, there is a desire for fluorinated surfactant-containing compositions which are effective in providing desired surfactant properties, and which eliminate more effectively from the body (including the composition and its degradation products).

It is expected that the fluorinated gemini surfactants of the present invention, which contain perfluorobutyl or perfluoropropyl groups, when exposed to biologic, thermal, oxidative, hydrolytic, and photolytic conditions found in the environment, will break down to various degradation products. For example, compositions comprising perfluorobutanesulfonamido groups are expected to degrade, at least to some extent, ultimately to perfluorobutanesulfonate salts. It has been surprisingly found that perfluorobutanesulfonate, tested in the form of its potassium salt, eliminates from the body more effectively than perfluorohexanesulfonate and much more effectively than perfluorooctanesulfonate.

Fluorinated gemini surfactants according to the present invention may be used in aqueous or non-aqueous compositions, and are typically effective for lowering the surface tension of formulations containing organic solvents and/or water. Uses of fluorinated gemini surfactants according to the present invention include, for example, as a defoamer emulsifier, dispersant, wetting aid, or leveling aid. In some embodiments, fluorinated gemini surfactants according to the present invention may be included in aqueous compositions, including those having dispersed polymeric latex particles (e.g., acrylic latex particles) therein.

Objects and advantages of this invention are further illustrated by the following non-limiting examples, but the particular materials and amounts thereof recited in these examples, as well as other conditions and, details, should not be construed to unduly limit this invention.

EXAMPLES

Unless otherwise noted, all parts, percentages, ratios, etc. in the examples and the rest of the specification are by weight, and all reagents used in the examples were obtained, or are available, from general chemical suppliers such as, for example, Sigma-Aldrich Company, Saint Louis, Mo., or may be synthesized by conventional methods.

Surface Tension

All products were diluted to the indicated concentration using deionized water. Static surface tension was measured using a Kruss K-12 tensiometer and the Du Nouy ring method at 20° C. Dynamic surface tensions were measured at the same concentration using a Sensadyne 5000 Maximum Bubble Pressure Tensiometer (available from Data Physics Instruments, Germany) at a bubble speed of 4 bubbles/second at 20° C.

Preparation of $C_4F_9SO_2N(CH_3)CH_2CH_2N^+(CH_3)_2$
$CH_2C_6H_4CH_2N^+(CH_3)_2$-$CH_2CH_2N(CH_3)SO_2C_4F_9$
$(Cl^-)_2$ (GS1)

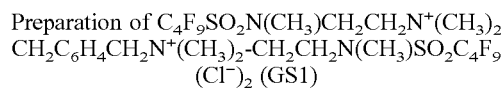

A solution of 28.8 grams (g) of dimethylaminoethyl chloride hydrochloride, 62.6 g of $C_4F_9SO_2NHCH_3$ (prepared as described in U.S. Pat. No. 6,664,354 (Savu, et al.) Example 1, Part A), 40 g of 50 weight percent aqueous NaOH, and 100 mL of tetrahydrofuran was stirred at reflux for 2.5 hours (hr). Gas-liquid chromatography showed complete conversion. The mixture was washed with water, extracted with methylene chloride, and stripped to give 49.3 g of material. Distillation of the material gave $C_4F_9SO_2N$ $(CH_3)CH_2CH_2N(CH_3)_2$ at 120° C./0.2 mm Hg (30 Pa), gave 45.0 g of a tan liquid that solidified on standing. A solution of 7.7 g of the solidified tan liquid and 1.75 g of 1,4-bis (chloromethyl)benzene in 10 mL acetonitrile gave a precipitate immediately on heating on steam bath. More acetonitrile (15 mL) was added and the mixture was heated at 50–60° C. for 8 hr, then diluted with 75 mL of diethyl ether, and filtered and dried to give 7.4 g of GS1 as a white salt. Static surface tension in deionized water was: 31.5 dyne/cm (0.315 millinewton/cm) at a concentration of 25.3 parts per million by weight (ppm); 21.0 dyne/cm (0.210 millinewton/cm) at a concentration of 65.1 ppm; 19.5 dyne/cm (0.195 millinewton/cm) at a concentration of 127.6 ppm. Dynamic surface tension of GS1 at a concentration of 0.5 percent by weight in water was 20.5 dyne/cm.

Evaluation of GS1 in Floor Finish

An aqueous styrene-acrylic emulsion floor finish was obtained from Cook Composites and Polymers, Kansas City, Mo., that was identical to that marketed by Cook Composites and Polymers under the trade designation "SHIELD-8"; except that the fluorinated surfactant (available under the trade designation "ZONYL FSN" from E. I. du Pont de Nemours & Co., Wilmington, Del.) and the hydrosol emulsion leveler (available under the trade designation "ESI-CRYL 842" from Cook Composites and Polymers) were omitted. Samples of this floor finish (i.e., FF1) were prepared for testing by addition of 100 ppm or 200 ppm levels of GS1, or a comparative fluorinated surfactant used in commercial floor finishes (i.e., "FLUORAD FC-129" surfactant from 3M Company).

Five mL of the liquid floor finish, containing 100 or 200 ppm of fluorochemical surfactant was applied to the center of a 12"×12" pre-cleaned black vinyl composite floor tile, then spread using a with a piece of gauze or cheesecloth covering the entire surface area of the tile until an even coating was obtained. The coating was applied using figure eight-shaped strokes covering the entire surface area of the tile until an even coating was obtained. An "X" was then made by wiping the floor finish between diagonally opposed corners of the tile. The process was repeated until a total of five layers of coating had been applied, allowing each coating layer to dry for at least 25–30 minutes prior to reapplication.

The floor tiles were coated with five courses of floor finish and the coated tiles were allowed to air dry for at least 7 days, then 60° gloss was measured using a BYK-Gardner gloss meter available under the trade designation "MICRO-TRI-GLOSS METER" from Paul N. Gardner Co., Inc., Pompano Beach, Fla., as taking the average of six different measurements over the coated surface of the tile. Gloss measurements are reported in Table 1 (below), and wherein "FS1" refers to a fluorinated surfactant obtained under the trade designation "FLUORAD FC-129" from 3M Company.

TABLE 1

| EXAMPLE | SURFACTANT | CONCENTRATION OF SURFACTANT | 60° GLOSS |
| --- | --- | --- | --- |
| FF1 | GS1 | 100 ppm | 79 |
| FF2 | GS1 | 200 ppm | 89 |
| Comparative 1 | FS1 | 100 ppm | 62 |
| Comparative 2 | FS1 | 200 ppm | 62 |

Various modifications and alterations of this invention may be made by those skilled in the art without departing from the scope and spirit of this invention, and it should be understood that this invention is not to be unduly limited to the illustrative embodiments set forth herein.

What is claimed is:

1. A gemini surfactant represented by the formula:

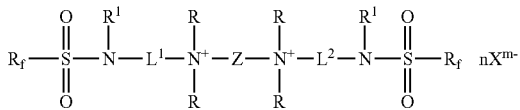

wherein
each $R_f$ independently represents perfluorobutyl or perfluoropropyl;
each $R^1$ independently represents alkyl having from 1 to 6 carbon atoms;
$L^1$ and $L^2$ represent alkylene having from 2 to 18 carbon atoms;
each R represents alkyl having from 1 to 6 carbon atoms;
Z represents an organic divalent linking group; and
$nX^{m-}$ represents an anion or anions having a charge m, wherein m and n are independently 1 or 2, and wherein the product of n and m is 2.

2. A gemini surfactant according to claim 1, wherein at least one $R_f$ is perfluorobutyl.

3. A gemini surfactant according to claim 1, wherein at least one of R or $R^1$ is methyl.

4. A gemini surfactant according to claim 1, wherein at least one L represents alkylene having from 2 to 4 carbon atoms.

5. A gemini surfactant according to claim 1, wherein at least one R represents methyl.

6. A gemini surfactant according to claim 1, wherein Z is selected from the group consisting of divalent hydrocarbylene groups having from 2 to 30 carbon atoms, and combinations of one or more hydrocarbylene groups having from 2 to 30 carbon atoms with at least one of at least one carbonyl, —O—, —S—, or —NR²—, wherein R² represents H or a hydrocarbyl group having from 1 to 12 carbon atoms.

7. A gemini surfactant according to claim 1, wherein Z represents hydrocarbylene.

8. A gemini surfactant according to claim 1, wherein Z represents

9. A gemini surfactant according to claim 1, wherein X is selected from the group consisting of halides, alkanesulfonates, arenesulfonates, hydroxide, alkanecarboxylates, and complex metal halides.

10. An aqueous composition comprising water and a gemini surfactant according to claim 1.

11. An aqueous composition according to claim 10, further comprising a dispersed polymeric latex.

12. A gemini surfactant according to claim 1, wherein the surfactant comprises at least one species having the formula

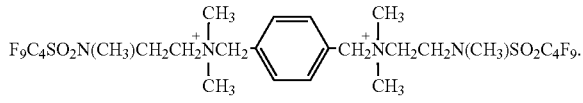

13. An aqueous composition comprising water and at least one gemini surfactant according to claim 1.

14. An aqueous composition according to claim 13, further comprising dispersed polymer particles.

15. An aqueous composition according to claim 14, wherein X is selected from the group consisting of halides, alkanesulfonates, arenesulfonates, hydroxide, alkanecarboxylates, and complex metal halides.

* * * * *